(12) United States Patent
Nokleby et al.

(10) Patent No.: US 10,293,344 B2
(45) Date of Patent: May 21, 2019

(54) SAMPLE HOLDER WITH MAGNETIC BASE AND MAGNETISABLE BODY

(71) Applicant: LIFE TECHNOLOGIES AS, Oslo (NO)

(72) Inventors: Lars Nokleby, Stabekk (NO); Berit Reed, Haslum (NO); Tine Hildisch, Oslo (NO); Axl Neurauter, Oslo (NO)

(73) Assignee: LIFE TECHNOLOGIES AS, Oslo (NO)

( * ) Notice: Subject to any disclaimer, the term of this patent is extended or adjusted under 35 U.S.C. 154(b) by 562 days.

(21) Appl. No.: 14/400,671

(22) PCT Filed: May 8, 2013

(86) PCT No.: PCT/EP2013/059675
§ 371 (c)(1),
(2) Date: Nov. 12, 2014

(87) PCT Pub. No.: WO2013/171123
PCT Pub. Date: Nov. 21, 2013

(65) Prior Publication Data
US 2015/0090664 A1    Apr. 2, 2015

(30) Foreign Application Priority Data

May 15, 2012    (GB) .................................. 1208547.8

(51) Int. Cl.
*B03C 1/14*    (2006.01)
*B03C 1/00*    (2006.01)
(Continued)

(52) U.S. Cl.
CPC ........................... *B03C 1/14* (2013.01); *B01L 9/06* (2013.01); *B03C 1/002* (2013.01); *B03C 1/025* (2013.01);
(Continued)

(58) Field of Classification Search
CPC .................. B03C 1/14; B03C 2201/18; B03C 1/28–1/286; B01L 9/06; B01L 9/52; B01L 9/523; G01N 35/0098; H01F 7/0263
See application file for complete search history.

(56) References Cited

U.S. PATENT DOCUMENTS 6,672,458 B2 *   1/2004   Hansen ..................... B01L 7/52
                                                                209/224
7,829,026 B2 *  11/2010   Su ....................... G01N 35/0098
                                                                 422/50
(Continued)

FOREIGN PATENT DOCUMENTS

EP           0030086         6/1981
EP           0136126         4/1985
(Continued)

OTHER PUBLICATIONS

PCT/EP2013/059675, "International Search Report dated", Jul. 23, 2013, 4 Pages.

*Primary Examiner* — David C Mellon
*Assistant Examiner* — Liam Royce (57) ABSTRACT

This invention relates to a sample holder for isolating magnetically labelled particles from a non-magnetic medium in a plurality of samples. The holder comprises a magnetic base for applying a magnetic force to the magnetically labelled particles and a body which is mountable on the base and demountable therefrom. The body comprises an array of sample holding portions and a magnetizable member which is magnetically urged towards the magnetic base when the body is seated on the base, whereby the body is urged to remain seated on the base. The invention also relates to use of the sample holder to separate magnetic
(Continued)

particles from a non-magnetic medium and methods of performing such a separation.

12 Claims, 11 Drawing Sheets

(51) Int. Cl.
  *B03C 1/025* (2006.01)
  *B01L 9/06* (2006.01)
  *G01N 35/00* (2006.01)
  *B03C 1/033* (2006.01)
  *B03C 1/28* (2006.01)
(52) U.S. Cl.
  CPC .......... *B03C 1/0332* (2013.01); *B03C 1/0335* (2013.01); *B03C 1/288* (2013.01); *G01N 35/0098* (2013.01); *B03C 2201/18* (2013.01); *B03C 2201/26* (2013.01)

(56) References Cited

U.S. PATENT DOCUMENTS

| | | | |
|---|---|---|---|
| 9,227,199 B2* | 1/2016 | Ellis | B03C 1/288 |
| 2003/0146166 A1 | 8/2003 | Ras et al. | |
| 2004/0023222 A1* | 2/2004 | Russell | G01N 33/54326 |
| | | | 435/6.15 |
| 2007/0297950 A1* | 12/2007 | Hochstrasser | B01L 3/50853 |
| | | | 422/400 |
| 2009/0180931 A1* | 7/2009 | Silbert | G01N 35/0099 |
| | | | 422/63 |
| 2010/0264090 A1* | 10/2010 | Ellis | B03C 1/288 |
| | | | 210/695 |

FOREIGN PATENT DOCUMENTS

| | | |
|---|---|---|
| EP | 0977037 | 2/2000 |
| WO | WO-1990/014891 | 12/1990 |
| WO | WO-2005/015216 | 2/2005 |
| WO | WO-2008/145712 | 12/2008 |
| WO | WO-2010/125170 | 11/2010 |

* cited by examiner

SAMPLE HOLDER WITH MAGNETIC BASE AND MAGNETISABLE BODY

CROSS-REFERENCE TO RELATED APPLICATIONS

This application is a U.S. 371 national phase of International application no. PCT/EP2013/059675 filed May 8, 2013, which claims priority to GB application no. 1208547.8 filed May 15, 2012, which disclosures are herein incorporated by reference in their entirety.

This invention relates to a sample holder for isolating magnetically labelled particles from a non-magnetic medium. The sample holder has a body and a magnetic base. The invention also relates to the body and magnetic base and use of the body and magnetic base in methods of isolating magnetically labeled particles from non-magnetic media.

BACKGROUND

The use of a high-gradient magnetic field to separate magnetically attractable particles from a fluid in which they are suspended is well known. Moreover, magnetic separation devices are used in a variety of industries including pharmaceutical, medical, agricultural, scientific and engineering fields. For example in biotechnology, a high-gradient magnetic field may be used to separate magnetically labelled bone marrow cells from a blood sample.

WO 90/14891 DYNAL A.S. discloses a conventional magnetic separation device whereby a test-tube/sample vessel, containing a fluid in which magnetically labelled particles are suspended, is arranged adjacent a strong magnet. The labelled particles are magnetically attracted to the side of the test-tube nearest the magnet. Thus, the supernatant is easily removable from the test-tube using a pipette whilst the magnetically labelled particles are left in the tube.

In order to save time, it is often desirable to process a large number of samples at once using a linear rack-like arrangement or tray-like arrangement. For example, the magnetic separating device disclosed in WO 90/14891 DYNAL A.S. comprises a rack for supporting a plurality of specimen containers. At least one magnet is arranged adjacent the rear portion of each test-tube such that the magnetic particles are attracted and adhere to the inside surface of the test-tube nearest the magnet; i.e. the interior surface at the rear of the sample vessel.

In the separation protocols, it is often important that the particles are able to freely mix with the fluid prior to magnetic separation. It is therefore desirable for magnetic separation devices to be designed such that the portion that holds the sample is separable from the portion which houses the magnet. For such devices with separable portions, it is important that the portion holding the sample and portion housing the magnet are sufficiently fixed together during magnetic separation to provide efficient separation of the magnetic particles and fluid.

WO 2008/145712 Invitrogen Dynal A/S provides a magnetic separation device with a sample vessel retaining portion that is releasably mounted on the magnetising portion, with the sample vessel retaining portion configured as a female portion that receives the male magnetizing portion. In this arrangement a user needs to be careful when inverting the device during magnetic separation, to avoid any release of the sample vessel retaining portion from the magnetizing portion.

Commercial devices provide similar simple mechanical arrangements, for example the AXYGEN® IMAG™ MSD 12-tube magnetic separation device provides a male/female mounting arrangement to retain a top portion, which holds the sample tubes, in a magnetic base. A variant designed to work with 96 well microplates utilizes adjustable clips to hold the microplate in place, however this requires the user to manually adjust the clips to ensure that the microplate is retained the optimal separation occurs, adding to the complexity of the process. Incorrect adjustment of mechanical clips may result in non-optimal separation. In addition, mechanical clips are subject to wear, and worn clips may not operate effectively.

There is therefore a need for improved designs for magnetic separation devices that can alleviate and/or overcome at least some of the above-mentioned problems. More specifically, the invention seeks to provide a magnetic separation device with a sample holding portion that is releasably attached to the portion which houses the magnet in a manner which is more effective than the prior art. In particular, the invention seeks to provide a device with an releasable attachment mechanism that is easy to use and highly effective.

BRIEF SUMMARY OF THE DISCLOSURE

In accordance with a first aspect of the present invention there is provided a sample holder for isolating magnetically labeled particles from a non-magnetic medium in a plurality of samples. The holder comprises a magnetic base for applying a magnetic force to the magnetically labeled particules and a body which is mountable on the base and demountable therefrom. The body comprises an array of sample holding portions. The body comprises a magnetisable member which is magnetically urged towards the magnetic base when the body is seated on the base, whereby the body is urged to remain seated on the base.

In a second aspect the invention provides a body as defined in the first aspect.

In a third aspect the invention provides use of a sample holder of the invention, when the body is seated on the base, to separate magnetically labelled particles from a non-magnetic medium in a sample held by a said sample holding portion.

In a fourth aspect the invention provides a method for separation of magnetically labelled particles from a non-magnetic medium in at least one sample. The method comprises placing the or each of the plurality of samples in a sample holding portion of a sample holder of the invention. Before or after placing the or each sample in a sample holding portion, the body is seated on the base. The magnetically labelled particles are then allowed to be separated from the non-magnetic medium by the action of the magnetic force applied to the particles by the base.

BRIEF DESCRIPTION OF THE DRAWINGS

Embodiments of the invention are further described hereinafter with reference to the accompanying drawings, in which.

DETAILED DESCRIPTION

Throughout the description and claims of this specification, the words "comprise" and "contain" and variations of them mean "including but not limited to", and they are not intended to and do not exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification including any accompanying claims, abstract and drawings, and/or all of the steps of any method or process so disclosed, may be combined in any combination, except combinations where at least some of such features and/or steps are mutually exclusive. The invention is not restricted to the details of any specific embodiments. The invention extends to any novel one, or any novel combination, of the features disclosed in this specification including any accompanying claims, abstract and drawings, or to any novel one, or any novel combination, of the steps of any method or process so disclosed.

The reader's attention is directed to all papers and documents which are filed concurrently with or previous to this specification in connection with this application and which are open to public inspection with this specification, and the contents of all such papers and documents are incorporated herein by reference.

All publications, patent applications, patents, and other references mentioned herein are incorporated by reference in their entirety. In case of conflict, the present specification, including definitions, will control.

The present invention includes a sample holder for isolating magnetically labelled particles from a non-magnetic medium (e.g. a non-magnetic liquid or solution) in a plurality of samples. The holder comprises a magnetic base for applying a magnetic force to the magnetically labelled particles and a body which is mountable on the base and demountable therefrom. The body comprises an array of sample holding portions. Each of the sample holding portions can hold a sample of the plurality of samples. Each sample may be in a sample vessel retained by a said sample holding portion; alternatively the sample holding portion may comprise a vessel for retaining a sample. The body comprises a magnetisable member which is magnetically urged towards the magnetic base when the body is seated on the base, whereby the body is urged to remain seated on the base.

The term "magnetisable" means "responds to a magnetic field". A "magnetisable member" therefore may be (or can comprise a material) selected from a permanent magnet, a ferromagnetic substance, ferrimagnetic substance and a paramagnetic substance. A magnetisable material can comprise one or more of iron, cobalt, nickel, and/or one or more rare earths. For example a magnetisable material can be or can comprise an alloy comprising one or more of iron, cobalt, nickel, and/or one or more rare earths.

The term "magnetically labeled" means responds to a magnetic field. Therefore "magnetically labeled particles" are particles that respond to a magnetic field. Such particles are disclosed in, for example, WO 2010/125170 and WO 2005/015216, (the contents of both of which are incorporated herein by reference). The particles may be monodisperse. By "monodisperse" is meant that for a plurality of particles (e. g. at least 100, more preferably at least 1000) the particles have a coefficient of variation (CV) of their diameters of less than 20%, for example less than 15%, typically of less than 10%. The particles can have a z-average diameter of no more than 10 μm, for example of no more than 5 μm or of no more than 1 μm. The z-average diameter can be measured by photon correlation spectroscopy.

Figure 1:
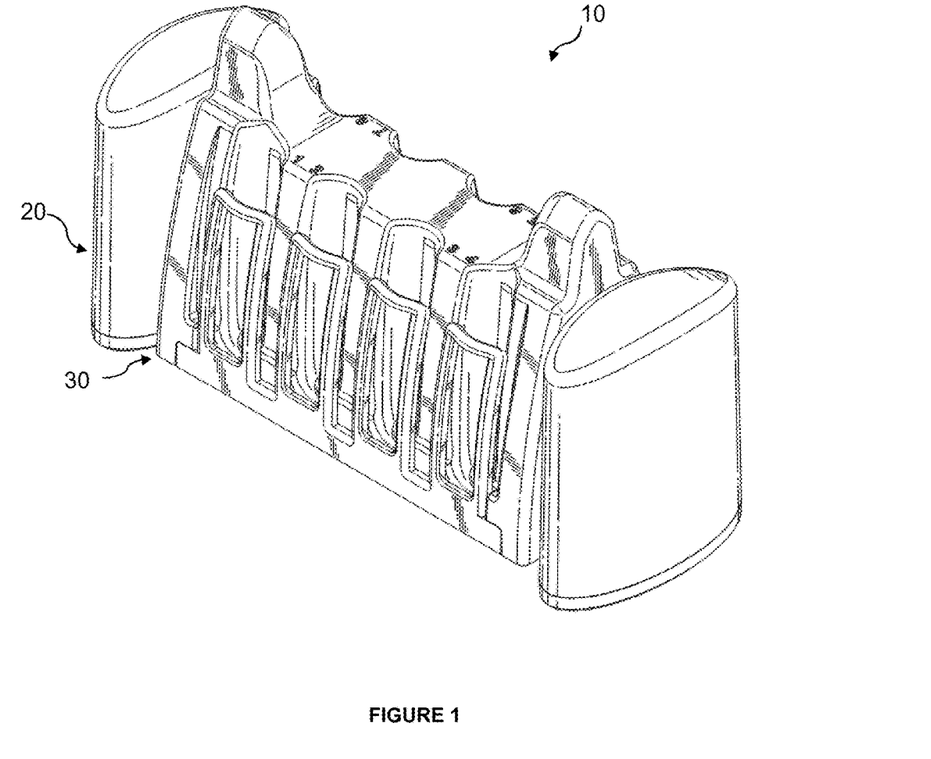
FIG. 1 is a front perspective view of a magnetic separation rack of the invention with the sample rack assembled to the magnetising base.
Figure 2A:
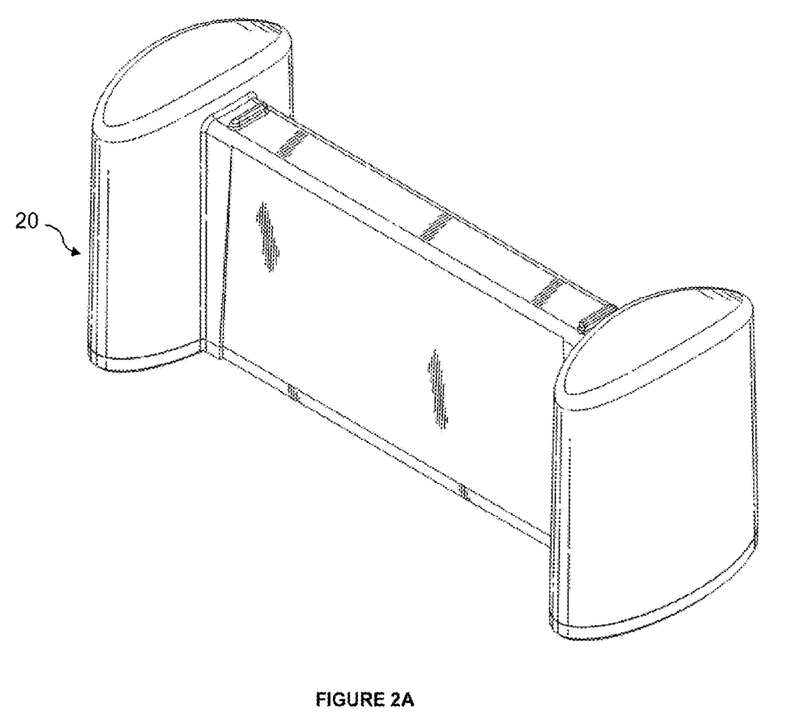
FIG. 2A is a front perspective view of the magnetising base of FIG. 1 when separated from the sample rack.
Figure 2B:
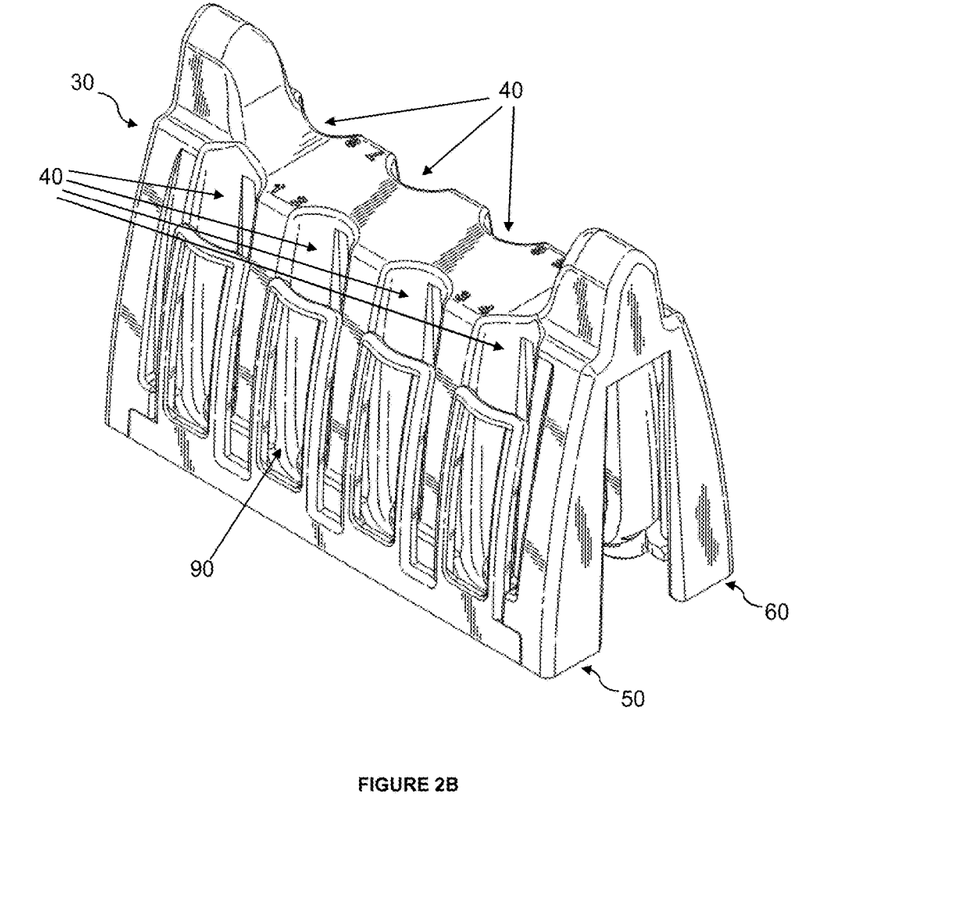
FIG. 2B is a front perspective view of the sample rack of FIG. 1 when separated from the magnetic base.

Referring now in detail to the Figures of the illustrated embodiments of the disclosure, FIGS. 1, 2A and 2B provide a perspective view of a sample holder 10 of the invention. The sample holder 10 is suitable for isolating magnetically labelled particles from a non-magnetic medium in a plurality of samples. The holder 10 comprises a magnetic or magnetising base 20 (for the purposes of this disclosure, the terms "magnetic base" and "magnetising base" are used interchangeably) for applying a magnetic force to the magnetically labelled particles. The holder 10 also comprises a body that may be a sample rack 30. In FIG. 1 the sample rack 30 is mounted on the magnetising base 20, whilst in FIG. 2 the sample rack 30 is separated from the magnetising base 20. The body comprises a magnetisable member 100 which is magnetically urged towards the base 20 when the body (e.g. rack 30) is seated on the base; in this way, the body is urged to remain seated on the base. The magnetizing base 20 may comprise at least one high-gradient magnetic assembly. The sample rack may comprise two opposed arms, each containing a row of sample holding portions, with the opposed arms being interconnected at an upper portion thereof by a bridge portion adapted to be seated on the base. As shown in the Figures, the sample rack 30 may comprise an array of sample vessel retaining portions 40, arranged in two parallel rows 50, 60 disposed in respective arms connected by a bridge portion 65 in an upper portion of the sample rack 30. This geometry has advantages, for example it makes efficient for use of the magnetic field provided by the base 20, when the base has a rectangular geometry. The sample rack 30 may comprise alternative arrays of sample vessel retaining portions. For example, the sample rack may comprise a single row of vessel retaining portions.

The sample rack and the magnetic base may have other geometries. If the base has a different geometry than rectangular as shown, the sample rack can have a complementary geometry with a bridge and an array of sample vessel retaining portions. For example, the base could have a circular geometry or ellipsoid geometry. For base with a circular geometry, the sample vessel retaining portions may be arranged in a circular or arcuate array. For a base with an ellipsoid geometry, the sample vessel retaining portions may be arranged in an elipsoid or arcuate array.

The body may be a multiple well plate, such as a microtitre plate (e.g. a standard or deep well microtitre plate), instead of a rack. For example, the body may be selected from multiple well plates and/or microtitre plates with 6, 24, 48, 96, 384 or 1536 wells.

Returning to FIGS. 1, 2A and 2B, the sample rack 30 comprises a frame that can be made of any suitable material. "Suitable material" in the context of the frame means any material that is predominantly not magnetic or magnetisable. As the frame is predominantly not magnetic or magnetisable, the frame has a negligible effect on any magnetic fields. The frame of the sample rack may be formed from a plastics material, e.g. a thermoplastic material, such as an olefin polymer or co-polymer, or a styrene polymer or co-polymer, or a polycarbonate. For example the frame or body of the sample rack may comprise or consist of acrylonitrile butadiene styrene (ABS). The frame of the sample rack may be formed from a metal that is not magnetic or magnetisable, e.g. the frame or body of the sample rack may comprise or consist of aluminium.

The high-gradient magnetic assembly of the magnetic base 20, when present, is configured to provide a high-gradient magnetic field in regions proximate to the sample vessel retaining portions 40 when the rack 30 is fitted to the magnetic base 20. For example, the high-gradient magnetic assembly may comprise one or more magnets oriented such that the north and south poles of the one or more magnets are proximate to the sample vessel retaining portions 40 when the rack 30 is fitted to the magnetic base 20. The magnetic base 20 therefore suitably provides a high-gradient magnetic field that is suitable for attracting and separating magnetically labelled particles from fluid in which they are contained. Further details of magnetic assemblies suitable for use in a magnetic base of the present invention are provided, for example, in WO 2008/145712 (the contents of which are incorporated herein by reference), in particular at page 10, line 15 to page 19, line 26.

The high-gradient magnetic assembly may comprise one or more permanent magnets. The high-gradient magnetic assembly may comprise one or more electromagnets. An electromagnet only provides a magnetic field when switched "on". Thus, the skilled person will appreciate that, when an electromagnet is switched "off", the magnetising portion does not provide a magnetic field from the electromagnet. In addition to "on" and "off" functionality, the magnetic field provided by an electromagnet may be adjusted by controlling the amount of current in the electromagnet when it is "on". The high-gradient magnetic assembly may comprise one or more electromagnets. When the electromagnet is "off" the magnetisable member may not be urged to remain seated on the base, and when the electromagnet is "on" the magnetisable member may be urged to remain seated on the base. Switching the electromagnet from the "off" to "on" states, and/or "on" to "off" states, and/or control of the amount of the current in the "on" state may be done manually or by automation.

The magnetic base may comprise one or more magnets to provide the magnetic field for isolating magnetically labeled particles from a non-magnetic medium, (e.g. providing a high-gradient magnetic field in the regions proximate to the sample vessel retaining portions), when the body is seated on the base. The magnetic base may comprise one or more magnets to exert a magnetic force on the magnetisable member(s), when the body is seated on the base. The magnetic force acts on the magnetisable member(s) to magnetically urge the magnetisable member(s) (and thus the body) towards the magnetic base.

The one or more magnets that provide the magnetic field for isolating the magnetically labeled particles and the one or more magnets that exert the magnetic force on the magnetisable member(s) may be the same or different. The same one or more magnets may provide for isolating magnetically labeled particles and urging the body to remain seated on the base. When the one or more magnets are the same, an advantage of synergy is provided. Different one or more magnets may provide isolation of magnetically labeled particles and urging the body to remain seated on the base; e.g. a first set of one or more magnets may provide the isolating and a second set of one or more magnets may urge the body to remain seated on the base. When the one or more magnets are different, decoupling is provided.

Figure 3:
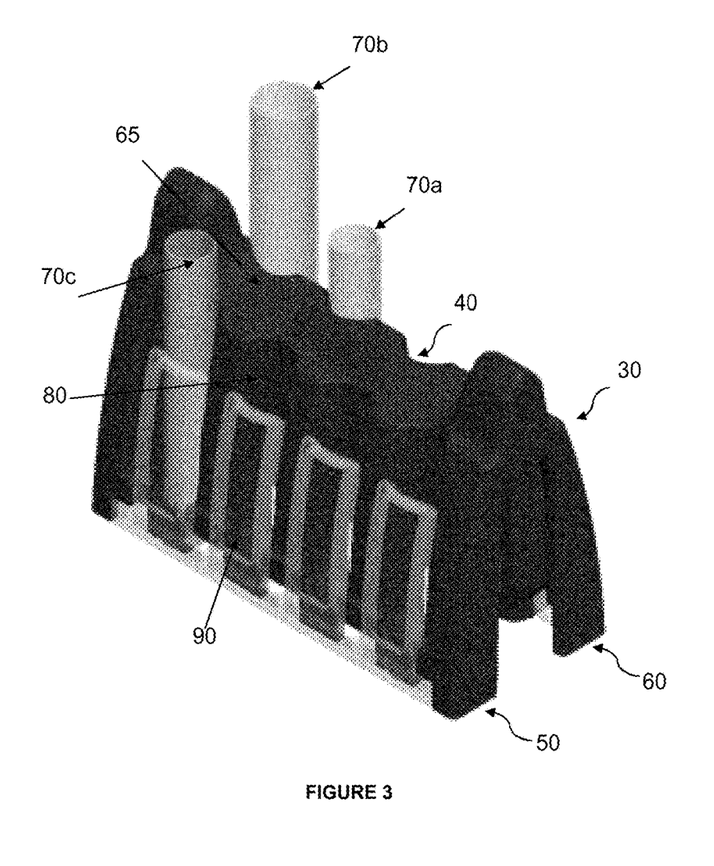
FIG. 3 is a front perspective view of a sample rack, illustrating retention of several sample tubes.

FIG. 3 demonstrates how sample tubes 70a, 70b, 70c can be positioned in the sample vessel retaining portions 40. The sample vessel retaining portions 40 may therefore each comprise a cavity 80 and a retention member 90 as shown in FIG. 3. The retention member 90 may be predominantly not magnetic or not magnetisable. The retention member 90 may be formed from a plastics material, e.g. a thermoplastic material, such as an olefin polymer or co-polymer, or a styrene polymer or co-polymer, or a polycarbonate. For example the retention member 90 may comprise or consist of polycarbonate or ABS. The retention member 90 may comprise or consist of a resilient material and therefore can press the sample tubes 70a, 70b, 70c against the portion of the cavity 80 closest to the magnetizing base 20 when the sample rack 30 is seated on the magnetizing base 20. This ensures that any magnetic or magnetisable material in the sample tubes 70a-c experiences substantially the highest available magnetic field when the sample rack 30 is fitted to the base 20. The resilience of the retention member 90 also permits the use of sample tubes 70a-c of different diameters in the rack. For example, sample tube 70b has a larger diameter than sample tubes 70a and 70b.

Figure 4:
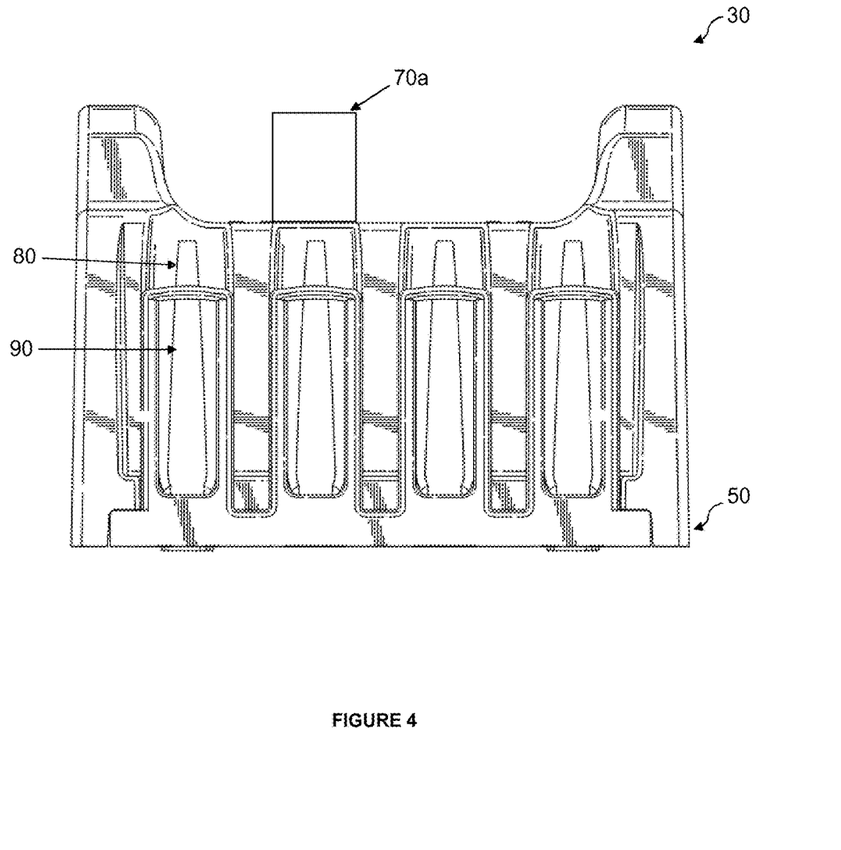
FIG. 4 is a front view of the sample rack of FIG. 3, illustrating retention of a sample tube.
Figure 5:
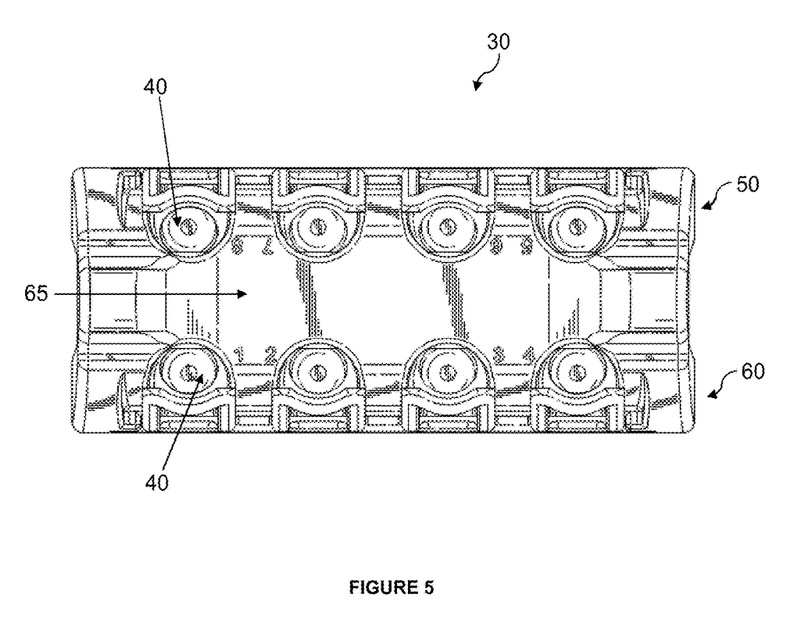
FIG. 5 is a top view of the sample rack of FIG. 3.
Figure 6:
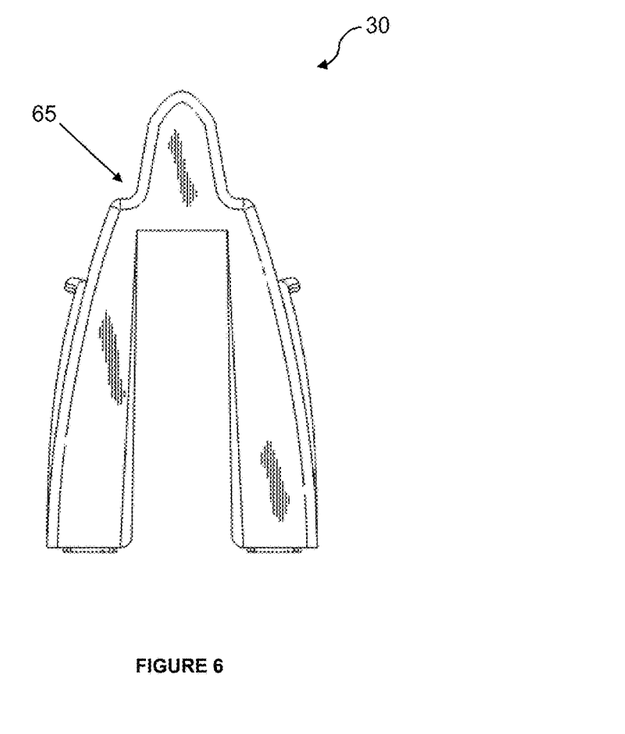
FIG. 6 is a right hand side view of the sample rack of FIG. 3.
Figure 7:
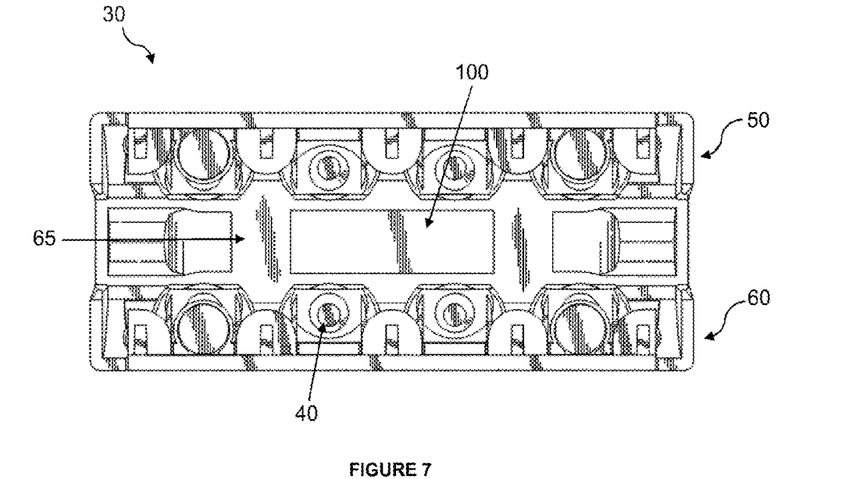
FIG. 7 is a bottom view of the sample rack of FIG. 3.

FIGS. 4 to 6 illustrate the sample rack 30 of FIG. 3 from front, side and top views respectively. FIG. 7 provides a bottom view of the sample rack 30, revealing the location of the magnetisable member 100. The magnetisable member 100 comprises a suitable magnetisable material, such as a magnet, or a ferromagnetic, ferromagnetic or paramagnetic material. For example, the magnetisable member can comprise a magnet or a magnetisable material; e.g. the magnetisable portion can comprise one or more of iron, cobalt, nickel, and/or one or more rare earths.

FIG. 7 illustrates the magnetisable member 100 (and hence magnetisable material) on the underside of the bridge portion 65. This has advantages for the illustrated embodiment, as the magnetisable material is remote from the sample vessel retaining portions 40. Without wishing to be bound by any theory, it is believed that such a location ensures that the magnetisable member 100 does not significantly influence the high-gradient magnetic field in the regions proximate to the sample vessel retaining portions 40 when the rack 30 is fitted to the magnetising base 20. In particular, the applicant has empirically determined that the magnetisable portion 100 does not have a detrimental effect on the efficiency of the magnetic separation of the magnetically labeled particles from the non-magnetic media. In addition, by locating the magnetisable material in the region of the bridge 65, the arrangement provides for effective mounting of the sample rack 30 on the magnetic base 20 with symmetric arrangement of the parallel rows 50, 60 of the sample vessel retaining portions 40 about the magnetising base 20.

The body, e.g. rack 30, of a sample holder of the invention may have a single magnetisable member or a plurality of magnetisable members. Where there is a plurality of magnetisable members in a rack 30 comprising a bridge portion, the bridge portion may comprise all the magnetisable members, e.g. in a generally symmetrical arrangement.

Additionally or alternatively to one or more magnetisable members located on the underside of a bridge portion, magnetisable member 100 may be located in many other portions of the body. For example, a magnetisable member (e.g. the sole magnetisable member(s) of a sample holder) may be located on at least a portion of the inside of one or more of the opposed arms. A magnetisable member may be embedded within the material of the frame, where the magnetisable member is isolated from the external environment; this has the advantage of protecting the magnetisable member from environmental damage, e.g. corrosion. A magnetisable member may be located on the topside of the bridge portion, side(s), or other part of the body. Where a magnetisable member is located on the topside of the bridge portion or other part of the body, the magnetisable member may, in some instances, be detachable from the body; this can be particularly advantageous where the body is a multiple well or microtitre plate. For example, detachability of the magnetisable member(s) permits the use of a multiple well or microtitre plate that can be disposable, and a magnetisable member that can be reusable. A detachable magnetisable member may be used to vary or adjust the strength with which the body is held to the base, e.g. by selection of the material and/or size and/or location of the or each detachable magnetisable member. Thus a detachable magnetic member may allow the degree with which the body is urged to remain seated on the base to be adjusted for specific experiments.

The material, size and location of the or each magnetisable member on the body can be selected to ensure that the magnetic force exerted by the base on the magnetisable member retains the body in seating arrangement on the base. This permits selection of the magnetic holding force predominantly independently of selection of the high-gradient magnetic field provided by the base. For example, the magnetic field provided by the base can be selected to optimise isolation of magnetically labelled particles from non-magnetic medium, while one or more of the material, size and location of the magnetisable member on the body can be selected to provide an optimal magnetic holding force between the body and the base. This can be advantageous when the same one or more magnets in the base provide the magnetic field for isolating magnetically labeled particles and the magnetic force on the magnetisable member(s) when the body is seated on the base.

The magnetic force exerted by the base on the magnetisable member of the body may retain the body in seated arrangement on the base when the sample holder is inverted. "Inverted" in this context means that the sample holder is tilted sufficiently to decant non-magnetic medium, if present, from one or more samples that may be present in the array of sample holding portions. For example, inverting can mean turning the sample holder upside down, that is rotating the sample holder by approximately 180°, thereby permitting removal of the non-magnetic medium. For example, inverting can mean rotating the sample holder by an angle of between about 95° and about 180°.

The sample holder of the present invention provide a number of advantages. For example, it provides a benefit of synergy: the magnetic field provided by the base, which in use isolates magnetically labelled particles from non-magnetic medium, is also utilised to retain the body in seated arrangement with the base. The system of the present invention, which utilises magnetic attraction between a magnetisable member on or in the body and magnetic field provided by the base to retain the body on the base, has the advantage of being relatively constant over time and relatively simple for a user to implement. This is different to mechanical methods for seating the body on the base, such as use of clips or clamping mechanisms, which are subject to wear over time, thereby decreasing the retaining force and/or requiring user adjustment.

Also provided is the use of the sample holder of the present disclosure to separate magnetically labelled particles from non-magnetic medium. In such a use the body is seated on the base.

Also provided are methods for the separation of magnetic particles from a non-magnetic medium as disclosed herein.

The particles to be isolated in a sample may be magnetically labelled using conventional magnetic labelling means. For example, the sample may be mixed with magnetic beads that bind to or coat the target particles of interest during a short incubation. The target substance may be, for example, DNA, RNA, mRNA, proteins, bacteria, viruses, sub-cellular components such as organelles (e.g. nuclei, mitochondria, multivessicular bodies, microvessicles), cells, enzymes, pesticides, hormones or other chemical compounds.

In operation, a sample (typically in solution) and a magnetically labeled particles are initially placed within a sample vessel, e.g. a sample tube 70a. The sample is then typically mixed and/or incubated. After mixing and/or incubation, a sample holder of the present disclosure may be used to isolate the magnetically labeled particles from the non-magnetic sample. The body (for example sample rack 30) is mounted on the magnetic base 20 such that the sample contained within the at least one sample vessel (e.g. sample tube 70a) is subject to a magnetic field, e.g. to a high-gradient magnetic field. During the magnetic separation period, the magnetically labelled particles are attracted by the magnetic field gradient and consequently migrate to a region of the internal surface of the sample vessel adjacent the magnetising portion. The body 30 is magnetically urged towards the base 20 by the magnetic force experienced by the magnetisable member 100. Any non-magnetic material may then be readily removed from the sample vessel, e.g. by decanting.

Figure 8:
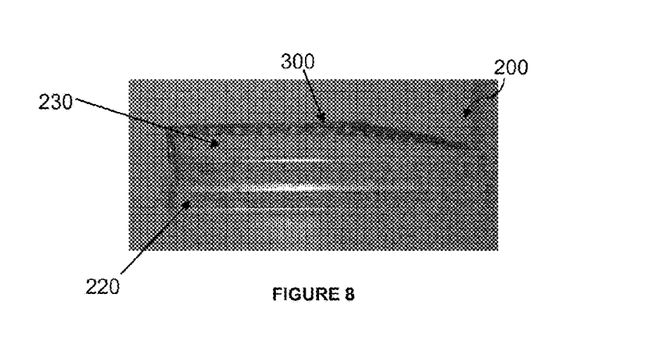
FIG. 8 is a front perspective view of a sample holder of the invention comprising a 96 well plate, magnetising base and magnetising member.
Figure 9:
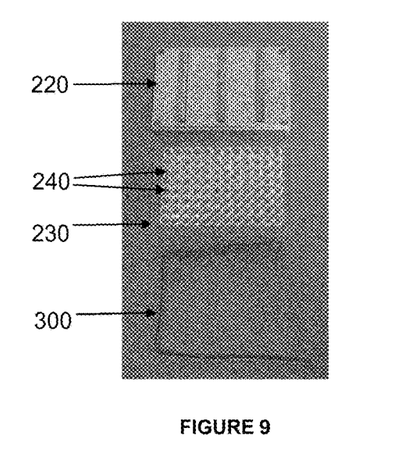
FIG. 9 is a top view of the sample holder of FIG. 8, when disassembled.

FIGS. 8 to 10 illustrate further embodiments of the disclosure. FIG. 8 is a front view of a sample holder 200 comprising a magnetic or magnetising base 220, body that is a 96 well plate 230 and magnetisable member 300, when assembled with the body seated on the base 220. FIG. 9 is a top view of the holder of FIG. 8, illustrating the base 200, 96 well plate 230 and magnetisable member 300 when disassembled. The base 220 is a magnetic device for deep well plates and is configured for standard sized 96 well plates to be seated thereupon. The base may comprise a high-gradient magnetic assembly as disclosed herein. The well plate 230 comprises 96 wells 240, which represent an array of sample holding portions. The magnetisable member 300 is a metal band.

Figure 10:
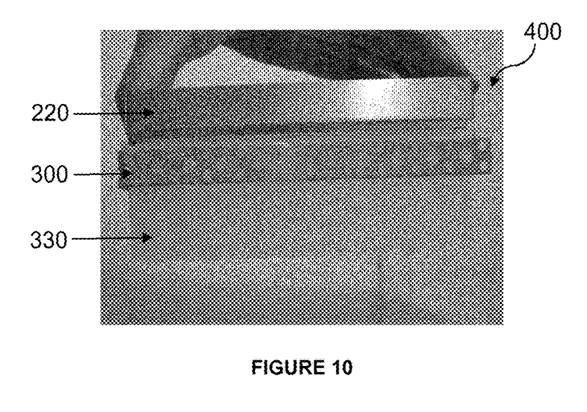
FIG. 10 is a front view of an inverted sample holder of the invention comprising a 96 well deep plate, magnetising base and magnetising member.

FIG. 10 illustrates another sample holder 400, when inverted. The sample holder 400 comprises the base 220 and magnetisable member 300 of FIGS. 8 and 9, but differs in that the body is a 96 deep well plate 330. FIGS. 8 to 10 therefore demonstrate that the same magnetic base 220 can be used with different bodies 230, 330. FIG. 10 also demonstrates that base 220 exerts sufficient force on the magnetisable member to retain the body in seated arrangement on the base when the sample holder is inverted. When the magnetisable member 300 is not present, inversion causes the deep well plate 330 to detach from the magnetic base 220. A similar effect of the magnetisable member 300 was demonstrated with the sample holder of FIG. 8 when it was inverted was inverted, i.e. well plate 230 was only retained on the base during inversion when magnetisable member 300 was present.

In a method of operation of the disclosure, a sample and magnetically labeled particles are initially placed within a sample vessel. The sample is incubated with the particles such that the particles are rosetted. During the incubation period, the sample contained within a sample vessel (for example a sample tube 70*a*) may be retained by a sample vessel retaining portion 40 of the body. The body can be separate from the magnetic base 20. If the magnetic base comprises one or more electromagnets, the electromagnets may be switched "off", in which case the body may be seated on the base during incubation.

During the incubation period, the sample may require mixing to help mix the magnetic labelling means and subsequently magnetically labelled particles within the sample. The body may therefore be configured such that it may be coupled to a mixing apparatus.

After incubation, a sample holder of the present disclosure may be used to isolate the magnetically labelled particles from the non-magnetic sample medium. The body (for example sample rack 30) is mounted on the magnetic base 20 such that the ample contained within the at least one sample vessel (e.g. sample tube 70*a*) is subject to a magnetic field, e.g. to a high-gradient magnetic field. During the magnetic separation period, the magnetically labelled particles are attracted by the magnetic field and consequently migrate to a region of the internal surface of the sample vessel adjacent the magnetising portion. The body 30 is magnetically urged towards the base 20 by the magnetic force experienced by the magnetisable member 100. This enables the easy removal of the non-magnetic supernatant, possibly using a pipette or by decanting, whilst the magnetically labelled particles are left isolated in the sample vessel. After washing, the target particles may be used in further studies (positive particle isolation). Magnetic separation may also be used to remove unwanted magnetic particles from a suspension such that substances remaining in the supernatant that is now depleted of the target particles can be used (negative isolation).

The magnetic separation device may be configured such that both the main volume and the tip of a sample vessel are subject to a high-gradient magnetic field, whereby the magnetic separation device is suitable for isolating magnetically labeled particles in both larger volumes and smaller volumes of a sample contained in the same sample vessel. For example, the magnetic separating device may process a sample which substantially fills the sample vessel by subjecting both the tip and main volume of a sample vessel, to a high-gradient magnetic field. After isolating the magnetically labelled particles and removing the supernatant, e.g. using a pipette, the magnetically labeled particles may be released/separated from the magnetic labelling means using a release-buffer. This may be achieved by adding a small volume of release-buffer to the isolated magnetically labelled particles remaining in the sample vessel. Hence, the same sample vessel may now contain only a small volume filling substantially the tip of the sample vessel. The magnetic separating device may then be used to subject the tip of the sample vessel to a high-gradient magnetic field such that the magnetic labelling means separate from the particles and migrate to a region of the internal surface of the sample vessel adjacent the magnetising portion. The particles released/separated from the magnetic labelling means may then be removed from the sample vessel, e.g. using a pipette.

The sample holders as herein described are inherently advantageous and as such may also be usefully used with any other suitable magnetic base or means to provide a suitable high-gradient magnetic field.

EXAMPLES

Example 1: Measurement of Magnetic Separation Efficiency

Measurements with a gauss meter indicated that, in the region of the sample vessel retaining portion 40 proximate (e.g. +/−1 to 3 mm) to the plane of the magnetisable member 100, the magnetisable member 100 caused a reduction in the magnetic field strength. The experiment of Example 1 was therefore conducted to determine the effect, if any, of this decrease in magnetic field strength on the magnetic separation efficiency of the sample rack.

Magnetic separation efficiency was measured determined with a sample holder of FIG. 1, when the sample rack 30 (sample rack A) was fitted to the base 20. The magnetisable member 100 was a metal plate. Comparative measurements were performed with an equivalent base and non-magnetic sample rack (sample rack B). The non-magnetic sample rack differed from sample rack 30 in that it did not have a magnetisable member.

Figure 11:
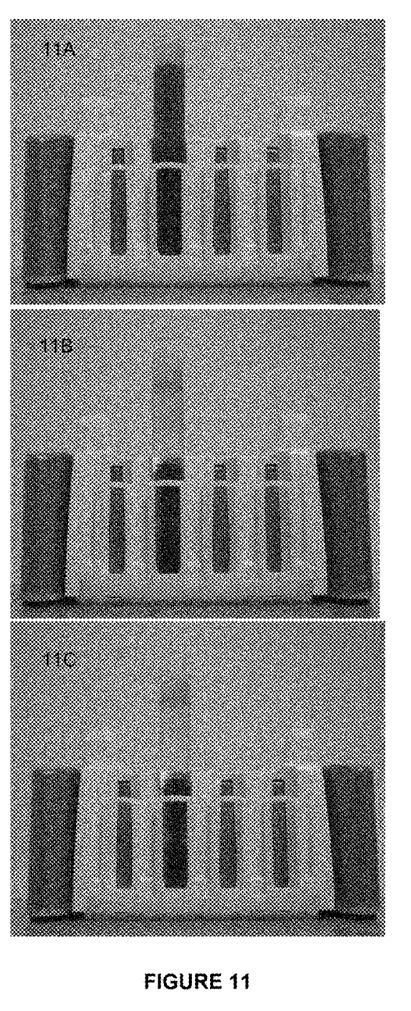
FIG. 11 is a series of photographs (11A to 11C) illustrating magnetic separation in a magnetic separation rack of the invention.
Figure 12:
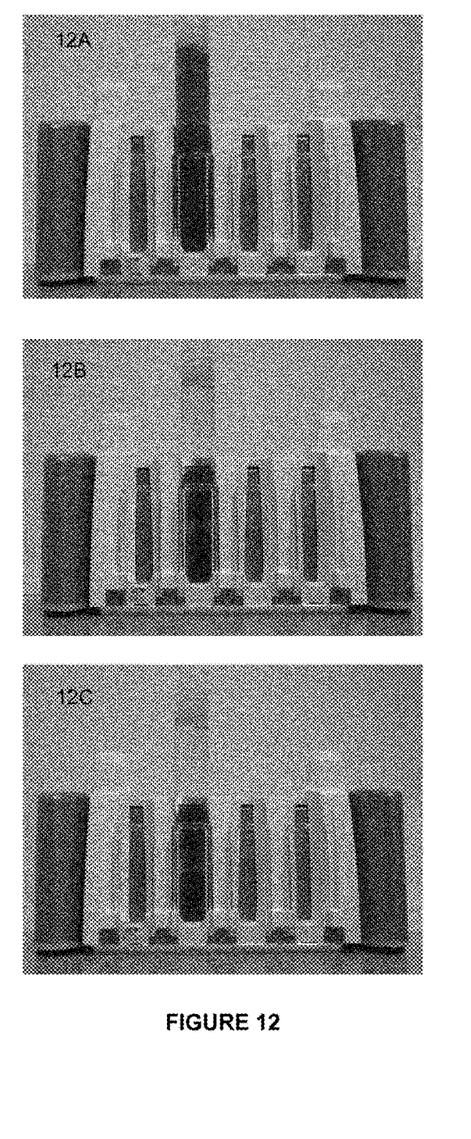
FIG. 12 is a series of photographs (12A to 12C) illustrating magnetic separation in a magnetic separation rack with a sample rack that does not have a magnetisable member.

The assessment of magnetic separation was performed with DYNABEADS® MYONE™ magnetic beads, available from Life Technologies Limited, Inchinnan Business Park, Paisley PA4 9RF, UK. Glass tubes (8 mL volume, 16 mm diameter) were filled with phosphate buffered saline (PBS) 0.1% bovine serum albumin (BSA) buffer containing the magnetic beads. The glass tubes were mixed well and placed in sample rack A and sample rack B. The solution in these glass tubes extended over 15 mm above the plane of the magnetisable member 100 in sample rack A. Thus the solution was subject to magnetic separation in the region of the sample vessel retaining portion 40 where the magnetisable member caused a reduction in the magnetic field strength, which may be expected to effect the efficiency of magnetic separation. Bead collection was monitored, with photographs taken at time intervals 0 (commencement of magnetic separation), 30 and 60 minutes. These results are illustrated in FIG. 11A to 11C for sample rack A, and FIG. 12A to 12C for sample rack B. FIGS. 11A and 12A were recorded at 0 minutes, FIGS. 12B and 13B represent 30 minutes, and FIGS. 11C and 12C represent 60 minutes.

A review of the figures indicated very similar bead capture when using the sample rack with the magnetisable metal plate (sample rack A) and without the magnetisable member (sample rack B). This indicates that the presence of the magnetisable member in the sample rack has little to no effect on the rate of bead collection compared to a conventional rack, notwithstanding the effect of the magnetisable member 100 on field strength in its vicinity. This demonstrates that sample racks of the invention provide efficient and effective isolation of magnetic particles from a non-magnetic medium.

In an embodiment the magnetisable member may be spatially arranged to be remote from the highest gradient region of the magnetic field, when the body is mounted on the magnetic base. In this arrangement the magnetisable member may have a negligible or no effect on the region of high magnetic field gradient, e.g. the region of the sample holding portion to which magnetically labeled particles would be attracted, when the body is mounted on the magnetic base. Therefore the presence of the magnetisable member may not affect the efficiency of the separation.

The invention claimed is:

1. A sample holder comprising:
a magnetic base comprising one or more high gradient magnets; and
a body which is mountable on the magnetic base and demountable therefrom, the body comprising an array of sample holding portions and at least one magnetisable member, the magnetisable member magnetically urged towards the magnetic base when the body is seated on the magnetic base, and wherein the same one or more high gradient magnets comprised in the magnetic base apply a magnetic force to a sample comprising magnetically labelled particles in a nonmagnetic medium and also magnetically urge the body to remain seated on the magnetic base when the sample holder is inverted;
wherein the body comprises two opposed arms, each containing a row of the array of sample holding portions, and wherein the opposed arms are interconnected at an upper portion thereof by a bridge portion adapted to be seated on the base;
wherein the bridge portion comprises the at least one magnetisable member.

2. The sample holder of claim 1, wherein the one or more high gradient magnets are selected from the group consisting of permanent magnets and electromagnets.

3. The sample holder of claim 1, wherein the one or more high gradient magnets comprises a plurality of magnets and the sample holder is adapted for the plurality of magnets to be juxtaposed to the plurality of samples when the body is seated on the magnetic base.

4. The sample holder of claim 1, wherein the magnetic base comprises a generally rectangular portion with two opposed walls upright and joined at the top by a top wall on which the body is adapted to be seated.

5. The sample holder of claim 1, wherein the body is a rack comprising twenty sample vessel retaining portions.

6. The sample holder of claim 5, wherein the at least one magnetisable member comprises a single magnetisable member which is disposed at a generally central position intermediate the ends of the rack.

7. The sample holder of claim 1, wherein the at least one magnetisable member comprises a plurality of magnetisable members, and wherein the bridge portion comprises the plurality of magnetisable members.

8. A method for separation of magnetically labelled particles from a nonmagnetic medium in a plurality of samples, comprising:
placing each of the plurality of samples in a sample holding portion of the array of sample holding portions of the sample holder of claim 1;
before or after placing the plurality of samples in the array of sample holding portions, seating the body on the magnetic base; and
allowing the magnetically labelled particles to be separated from the non-magnetic medium by application of the magnetic force to the magnetically labelled particles by the magnetic base.

9. The method of claim 8, wherein the magnetically labelled particles are magnetic polymer particles.

10. The method of claim 8, wherein the magnetically labelled particles have a z-average diameter of no more than 10 μm.

11. The method of claim 8, further comprising:
inverting the sample holder to dispense the non-magnetic medium from the array of sample holding portions while retaining the magnetically labelled particles.

12. The method of claim 11, wherein the magnetic force exerted by the magnetic base on the magnetisable member retains the body in a seated arrangement on the base during the inverting of the sample holder.

* * * * *